United States Patent [19]

Lussling et al.

[11] 4,283,337

[45] Aug. 11, 1981

[54] PROCESS FOR THE PURIFICATION OF TRYPTOPHANE AND DERIVATIVES OF TRYPTOPHANE

[75] Inventors: Theodor Lussling, Constance; Alfred Maierhofer, Allensbach; Paul Scherberich, Constance, all of Fed. Rep. of Germany

[73] Assignee: Deutsche Gold und- Silber-Scheideanstalt Vormals Roessler, Frankfurt, Fed. Rep. of Germany

[21] Appl. No.: 94,801

[22] Filed: Nov. 15, 1979

[30] Foreign Application Priority Data

Nov. 18, 1978 [DE] Fed. Rep. of Germany ....... 2850074

[51] Int. Cl.$^3$ .......................................... C07D 209/20
[52] U.S. Cl. ................. 260/326.14 T; 260/326.14 A; 260/701
[58] Field of Search ............. 260/326.14 T, 326.14 A, 260/701

[56] References Cited

U.S. PATENT DOCUMENTS

| | | | |
|---|---|---|---|
| 2,435,125 | 1/1948 | Britton et al. | 260/326.14 T |
| 2,565,354 | 1/1951 | Cohen | 260/701 |

OTHER PUBLICATIONS

Cotton et al., Adv. Inor. Chem., pp. 430 & 431, Interscience, N.Y. (1962).
Kirk-Othmer, Ency. of Chem. Tech., 2nd Ed., vol. 19, pp. 420 & 421 (1969).

*Primary Examiner*—Donald G. Daus
*Assistant Examiner*—D. B. Springer
*Attorney, Agent, or Firm*—Cushman, Darby & Cushman

[57] ABSTRACT

Tryptophane and tryptophane derivatives are purified by treating them in an inert solvent at a temperature between about 20° C. and the boiling point of the mixture with a salt of dithionous acid. Preferably there is used as solvent a mixture of water and a lower aliphatic carboxylic acid. Normally a single treatment results in a pure, colorless, satisfactory product.

14 Claims, No Drawings

4,283,337

PROCESS FOR THE PURIFICATION OF TRYPTOPHANE AND DERIVATIVES OF TRYPTOPHANE

BACKGROUND OF THE INVENTION

In the production of tryptophane and derivatives of tryptophane there generally result at first colored crude products whose conversion into highly pure products suitable for pharmaceutical purposes is expensive and makes necessary high loss purification operations.

SUMMARY OF THE INVENTION

The present invention overcomes this problem by purifying tryptophane and substituted tryptophanes in an inert solvent at a temperature between 20° C. and the boiling point of the mixture with a salt of dithionous acid (hydrosulfurous acid).

Surprisingly normally a single treatment according to the process of the invention results in a pure, colorless, unobjectionable product.

According to the process of the invention there can be purified both the racemate as well as the individual optical isomers. Examples of the materials which can be purified are tryptophane itself as well as ring substituted tryptophanes wherein the substituent is a halogen, e.g., fluorine, chlorine or bromine, alkyl, e.g., lower alkyl such as 1-4 carbon atoms, hydroxy or benzyloxy and N-acyl substituted tryptophane where the acyl is lower alkanoyl, N-haloalkanoyl (e.g., where the halogen is chlorine, bromine or fluorine), N-aroyl, N-arylsulfonyl or N-carbohydrocarbyloxy.

Examples of substrates to be purified are tryptophane itself, its ring substituted derivatives such as 5-chlortryptophane, 5-hydroxytryptophane, 5-methyltryptophane, 2-methyltryptophane, 2-hydroxytryptophane or 5-benzyloxytryptophane, or N-acylderivates, such as N-formyltryptophane, N-acetyltryptophane, N-chloroacetyltryptophane, N-dichloracetyltryptophane, N-trifluoracetyltryptophane, N-benzoyltryptophane, N-phthaloyltryptophane, N-p-toluenesulfonyltryptophane or N-carbobenzoxytryptophane.

Additional illustrative compounds are 5-bromotryptophane, 5-ethyltryptophane, 5-propyltryptophane, 5-butyltryptophane, N-propionyltryptophane, N-butyryltryptophane, N-bromoacetyltryptophane, N-benzensulfonyltryptophane, N-carbomethoxytryptophane and N-carboethoxytryptophane.

Suitable inert solvents are, for example, water, lower aliphatic alcohols, e.g. lower alkanols, e.g. with 1-4 carbon atoms such as methanol, ethanol, isopropyl alcohol or n-butanol; esters, e.g. lower alkyl esters of lower alkanoic acids, e.g., methyl acetate, ethyl acetate, propyl acetate, butyl acetate, methyl propionate, amyl acetate, or lower aliphatic carboxylic acids such as formic acid, acetic acid, propionic acid or butyric acid.

There can also be used mixtures of different solvents which are miscible with each other.

Preferred are mixtures of water and lower aliphatic carboxylic acids, e.g., formic acid, acetic acid and propionic acid. Particularly preferred is aqueous acetic acid. This can contain for example 20 to 95 weight percent acetic acid.

The treatment of the substrate according to the process of the invention is carried out at temperatures between about 20° C. and the boiling point of the mixture. According to a preferred method of operation the substrate to be purified together with the inert solvent and the salt of the dithionous acid are heated together at reflux temperatures for a short time, for example 5 to 30 minutes and then cooled to room temperature.

Thereby the purified product separates out.

As salts of dithionous acid there are of special importance the alkali metal salts, above all sodium dithionite. There can also be used for example potassium dithionite. The amount of salt of dithionous acid added depends on the degree of coloration or impurities of the substrate to be purified and generally amounts to about 0.5 to 5 weight percent based on the substrate employed.

The treatment of the substrate according to the process of the invention in a given case can take place in the additional presence of activated carbon. The amount of activated carbon likewise depends on the degree of impurities of the substrate to be purified and suitably amounts to about 5 to 20 weight percent based on the substrate employed.

Except for the yields and the permeability to light all percentages are weight percentages.

The process can comprise, consist essentially of or concist of the steps set forth and the materials employed can comprise, consist essentially of or consist of those set forth.

The process of the invention will be explained further in the following examples.

DESCRIPTION OF THE PREFERRED EMBODIMENTS

EXAMPLE 1

100 grams of N-acetyl-D,L-tryptophane having a content of 99% (determined by titration of the COOH groups) and a transparency of 94% (measured on an 0.1% solution in 1 N sodium hydroxide in a layer thickness of 1 cm at a wave length of 430 nm) and 2 grams of sodium dithionite were heated in 1,100 ml of 20% aqueous acetic acid for 15 minutes at reflux temperature and filtered hot.

After cooling to 20° C. there were obtained 92 grams (93% of theory based on the content of the material employed) of a colorless product which had a content of N-acetyl-D,L-tryptophane of 99.5% and a transparency of 99%.

EXAMPLE 2

100 grams of a light brown colorless N-acetyl-D,L-tryptophane having a content of 95% (determined by titration of the COOH groups) and a transparency of 88% (measured as in Example 1), 3 grams of sodium dithionite and 20 grams of activated carbon were treated in 1,100 ml of 20% aqueous acetic acid in the same manner as in Example 1.

There were obtained 86 grams (90% of theory based on the content of the material employed) of a colorless product which had an N-acetyl-D,L-tryptophane content of 99.8% and a transparency of 98.5%.

EXAMPLE 3

100 grams of a rose colored L-tryptophane having a content of 94% (determined by titration of the NH$_2$ group) and a transparency of 92% (measured of a 1% solution in 2 N hydrochloric acid in a layer thickness of 1 cm at a wave length of 430 nm), 2.5 grams of sodium dithionite and 15 grams of activated carbon were heated at reflux temperature for 15 minutes in 1,600 ml of 25% aqueous acetic acid and then filtered hot.

After cooling to room temperature there were obtained 85 grams (90% of theory based on the content of the material employed) of a colorless product which had a content of 99% of L-tryptophane and a transparency of 98.5%.

EXAMPLE 4

100 grams of D,L-tryptophane having a content of 96% (determined by titration of the $NH_2$ groups) and a transparency of 91% (measured on a 0.5% solution in 2 N-hydrochloric acid in a layer thickness of 1 cm at a wave length of 430 nm), 5 grams of sodium dithionite and 10 grams of activated carbon in 2,000 ml of 20% aqueous formic acid were heated at reflux temperature for 5 minutes and filtered hot.

After cooling to room temperature there were obtained 80 grams (83% of theory based on the content of the material employed) of a colorless product which had a content of D,L-tryptophane of 99.5% and a transparency of 97%.

EXAMPLE 5

100 grams of L-tryptophane having a content of 93% (determined by titration of the $NH_2$ groups) and a transparency of 90% (determined as in Example 3), 4 grams of sodium dithionite and 15 grams of activated carbon in a mixture of 2,500 ml of water, 500 ml of methanol and 200 ml of acetic acid were heated at reflux temperature for 15 minutes and filtered hot.

After cooling to room temperature there were obtained 80 grams (86% of theory based on the content of material employed) of pure, colorless L-tryptophane, which had an L-tryptophane content of 99.5% and a transparency of 99%.

EXAMPLE 6

100 grams of 5-hydroxy-L-tryptophane having a content of 95% (determined by titration of the $NH_2$ groups) and a transparency of 94% (determined as in Example 3), 4 grams of sodium dithionite and 10 grams of activated carbon in 1,200 ml of 25% aqueous acetic acid were heated at reflux temperature for 15 minutes and filtered hot.

After cooling to room temperature there were obtained 83 grams (87.5% of theory based on the content of the starting material) of a colorless product which had a content of 5-hydroxy-L-tryptophane of 99% and a transparency of 98.5%.

EXAMPLE 7

100 grams of N-benzoyl-D,L-tryptophane having a content of 96% (determined by titration of the COOH groups) and a transparency of 90% (determined as in Example 1), 5 grams of sodium dithionite and 20 grams of activated carbon in 1,500 ml of 25% aqueous acetic acid were heated at reflux temperature for 30 minutes and filtered hot.

After cooling to room temperature the yield of colorless product was 82 grams (85% of theory, based on the content of material employed), the content of N-benzoyl-D,L-tryptophane was 95% and the transparency 98.5%.

There is hereby incorporated by reference the entire disclosure of German priority application P 28 50 074.5-44.

What is claimed is:

1. In a process for purifying a substance which is (1) tryptophane or (2) tryptophane substituted in the 2 or 5 position of the ring by chlorine, bromine, fluorine, alkyl of 1–4 carbon atoms, hydroxy or benzyloxy or (3) tryptophane substituted on the $NH_2$ group by formyl, acetyl, chloroacetyl, fluoroacetyl, benzoyl, phthaloyl toluenesulfomyl or carbobenzoxy, the improvement consisting essentially of treating the substance to be purified in a solvent inert under the conditions of purification at a temperature between about 20° C. and the boiling point of the mixture with an alkali metal dithionite.

2. The process of claim 1 wherein there is purified (1) tryptophane or (2) tryptophane substituted in the 2 or 5 ring position by chlorine, hydroxy, methyl or benzyloxy or (3) tryptophane substituted on the $NH_2$ group by formyl, acetyl, chloroacetyl, fluoroacetyl, benzoyl, phthaloyl, toluenesulfonyl or carbobenzoxy.

3. The process of claim 1 wherein there is purified tryptophane 5-chlorotryptophane, 5-hydroxytryptophane, 5-methyltryptophane, 2-hydroxytryptophane or 5-benzyloxytryptophane, N-formyltryptophane, N-acetyltryptophane, N-chloroacetyltryptophane, N-dichloroacetyltryptophane, N-trifluoroacetyltryptophane, N-benzoyltryptophane, N-phthaloyltryptophane, N-p-toluenesulfonyltryptophane or N-carbobenzoxytryptophane.

4. The process of claim 3 wherein the solvent is water, a lower alkanol, a lower alkyl acetate or lower alkanoic acid or mixture thereof.

5. The process of claim 4 wherein the solvent is a mixture of water and a lower alkanoic acid.

6. The process of claim 5 wherein the salt is sodium dithionite.

7. The process of claim 6 wherein there is purified tryptophane, N-acetyl tryptophane, 5-hydroxy-tryptophane or N-benzoyl tryptophane.

8. The process of claim 7 wherein the solvent is a mixture of water and formic acid or acetic acid.

9. The process of claim 8 wherein the solvent is 80 to 5% water and 20 to 95% of formic acid or acetic acid.

10. The process of claim 1 wherein the solvent is a mixture of water and a lower alkanoic acid.

11. The process of claim 1 wherein the salt is sodium dithionite.

12. The process of claim 1 wherein the alkali metal dithionite is employed in an amount of 0.5 to 5.0 weight percent based on the weight of the substance.

13. The process of claim 4 wherein the solvent is water, a lower alkanol, methyl acetate, ethyl acetate, propyl acetate, butyl acetate, formic acid, acetic acid, propionic acid, butyric acid or a mixture thereof miscible with each other.

14. The process of claim 1 wherein there is also employed in the purifying treatment activated carbon.

* * * * *